(12) United States Patent
Rezach

(10) Patent No.: US 7,678,112 B2
(45) Date of Patent: Mar. 16, 2010

(54) OPEN DORSAL ADJUSTING CONNECTOR

(75) Inventor: Alan Rezach, Atoka, TN (US)

(73) Assignee: Warsaw Orthopedic, Inc.

( * ) Notice: Subject to any disclaimer, the term of this patent is extended or adjusted under 35 U.S.C. 154(b) by 635 days.

(21) Appl. No.: 11/114,405

(22) Filed: Apr. 26, 2005

(65) Prior Publication Data

US 2006/0241596 A1  Oct. 26, 2006

(51) Int. Cl.
*A61B 17/56* (2006.01)
(52) U.S. Cl. .................................................... 606/60
(58) Field of Classification Search .............. 606/60, 606/61, 72–73, 246, 250–279
See application file for complete search history.

(56) References Cited

U.S. PATENT DOCUMENTS

| | | | |
|---|---|---|---|
| 4,653,481 A | 3/1987 | Howland et al. | |
| 5,030,220 A | 7/1991 | Howland | |
| 5,047,029 A * | 9/1991 | Aebi et al. ................ | 606/61 |
| 5,084,048 A | 1/1992 | Jacob et al. | |
| 5,176,680 A | 1/1993 | Vignaud et al. | |
| 5,312,404 A | 5/1994 | Asher et al. | |
| 5,330,473 A | 7/1994 | Howland | |
| 5,476,463 A | 12/1995 | Boachie-Adjei et al. | |
| 5,582,612 A | 12/1996 | Lin | |
| 5,716,355 A | 2/1998 | Jackson et al. | |
| 5,743,907 A | 4/1998 | Asher et al. | |
| 5,910,142 A | 6/1999 | Tatar | |
| 5,938,663 A | 8/1999 | Petreto | |
| 5,984,924 A | 11/1999 | Asher et al. | |
| 6,123,706 A * | 9/2000 | Lange ........................ | 606/61 |
| 6,187,005 B1 * | 2/2001 | Brace et al. ................. | 606/61 |
| 6,413,258 B1 | 7/2002 | Bernhardt | |
| 6,482,207 B1 | 11/2002 | Errico | |
| 6,565,569 B1 | 5/2003 | Assaker et al. | |
| 6,569,164 B1 | 5/2003 | Assaker et al. | |
| 6,585,737 B1 | 7/2003 | Baccelli et al. | |
| 6,610,062 B2 | 8/2003 | Bailey et al. | |
| 6,623,485 B2 * | 9/2003 | Doubler et al. ............. | 606/61 |
| 6,626,906 B1 | 9/2003 | Young | |
| 6,673,074 B2 * | 1/2004 | Shluzas ...................... | 606/61 |
| 6,945,972 B2 | 9/2005 | Frigg et al. | |
| 2004/0087949 A1 * | 5/2004 | Bono et al. .................. | 606/61 |
| 2005/0137594 A1 * | 6/2005 | Doubler et al. ............. | 606/61 |
| 2005/0251141 A1 * | 11/2005 | Frigg et al. ................. | 606/61 |
| 2006/0036252 A1 * | 2/2006 | Baynham et al. ........... | 606/73 |

FOREIGN PATENT DOCUMENTS

| | | |
|---|---|---|
| DE | 92 15 561 U1 | 1/1993 |
| WO | WO 02/36026 A2 | 5/2002 |
| WO | WO 2005/122965 A | 12/2005 |

\* cited by examiner

*Primary Examiner*—Thomas C Barrett
*Assistant Examiner*—Michael J Araj

(57) ABSTRACT

An apparatus for connecting an implant with a rod comprises a body, a collet, an annular ring member, a washer, and a nut. The body defines a first channel to receive the rod and a second channel extending through the body. The collet is positionable in the second channel and defines an aperture for receipt of the implant. The ring member includes a gap and defines an aperture for receipt of the collet. The washer is positionable adjacent the second channel and is configured to translate along the body to allow pivoting of the collet relative to the body. The nut is operable to connect with the collet to move the collet within the second channel. Movement of the collet is operable to expand the ring member and contract the collet around the implant to secure the implant at a desired position.

27 Claims, 6 Drawing Sheets

OPEN DORSAL ADJUSTING CONNECTOR

BACKGROUND OF THE INVENTION

The present invention generally relates to an open dorsal adjusting connector apparatus used for connection of implants with spinal rods. The apparatus can be useful for correction of spinal injuries or deformities, and more specifically, but not exclusively, concerns apparatuses allowing for mutually exclusive connection between implants and rods, as well as permitting dorsal height adjustment.

In the realm of orthopedic surgery, it is well known to use implants to fix the position of bones. In this way, the healing of a broken bone can be promoted, and malformations or other injuries can be corrected. For example, in the field of spinal surgery, it is well known to place such implants into vertebrae for a number of reasons, including (a) correcting an abnormal curvature of the spine, including a scoliotic curvature, (b) to maintain appropriate spacing and provide support to broken or otherwise injured vertebrae, and (c) perform other therapies on the spinal column.

Typical implant and connection systems include several pieces, which commonly are useful and may be associated with only specific other pieces. Bone screws, hooks, and clamps are well known as fixation devices, which are connected or adjoined to a particular bone as a connection between the bone and the connection system which can include a support and/or stabilizing member such as a spinal rod. In such a system, a series of two or more screws may be inserted into two or more vertebrae to be instrumented. A rod is then placed within or coupled to the screws, or is placed within a connecting device that links the rod and a screw, and the connections are tightened. In this way, a rigid supporting structure is fixed to the vertebrae, with the rod providing the support that promotes correction or healing of the vertebral malformation or injury by keeping the vertebrae in a particular position.

DESCRIPTION OF THE ILLUSTRATED EMBODIMENTS

Figure 1:
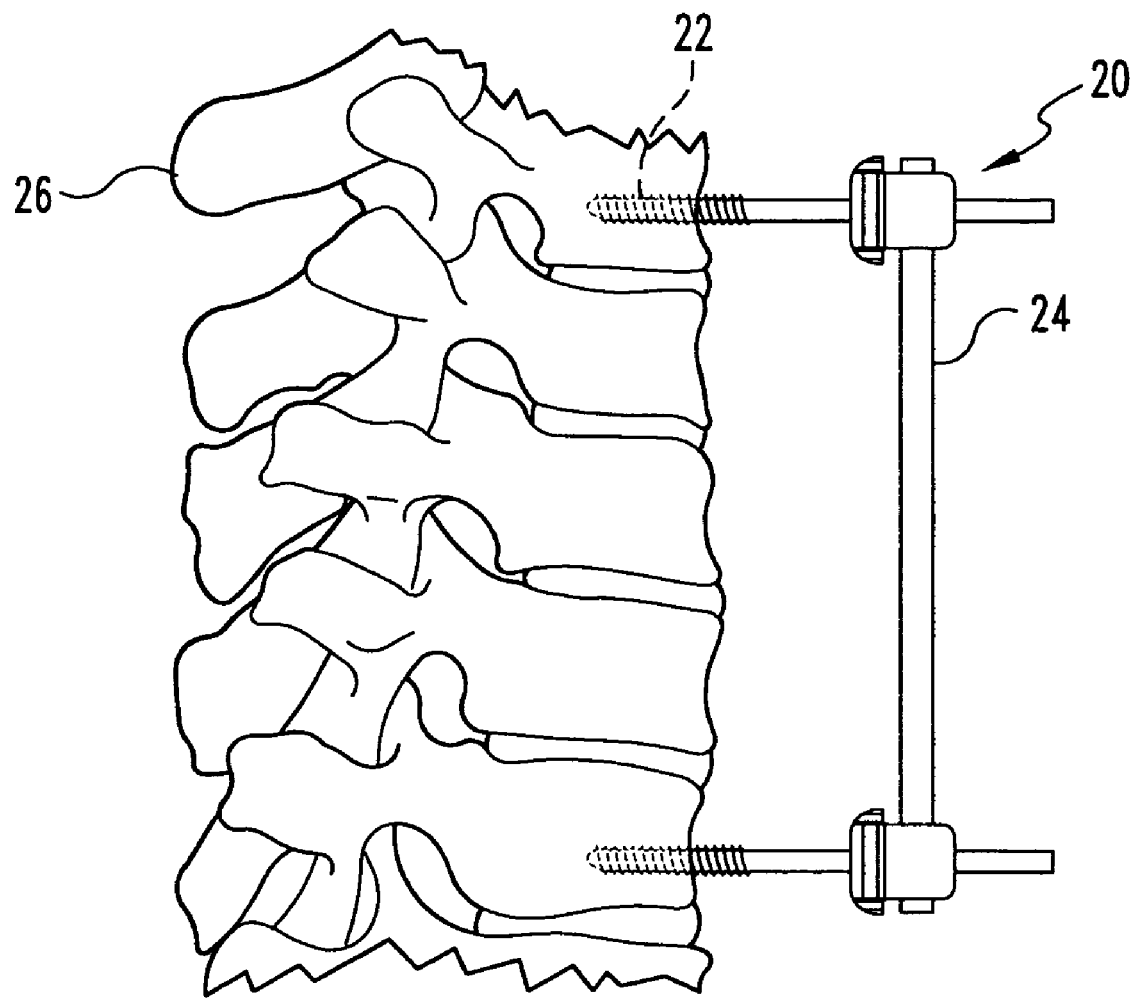
FIG. 1 is a perspective view of a connecting assembly relative to vertebrae according to one disclosed embodiment.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Referring to FIG. 1, there is shown an embodiment of a connecting assembly 20. Connecting assembly 20 is operable to connect an implant 22, such as a Schanz-type screw with a threaded anchoring portion, with an elongated member 24, such as a spinal rod. In the illustrated embodiment, implant 22 is inserted into a vertebra 26 and member 24 is utilized to maintain one or more vertebrae at a desired position. However, it should be appreciated that the implant utilized in conjunction with connecting assembly 20 can be any appropriate bone anchor or bone-engaging mechanism. Additionally, member 24 can be any appropriate elongated member such as a bar, connector, or other orthopedic construct. Further, member 24 may have one of a number of desired lengths.

Figure 2:
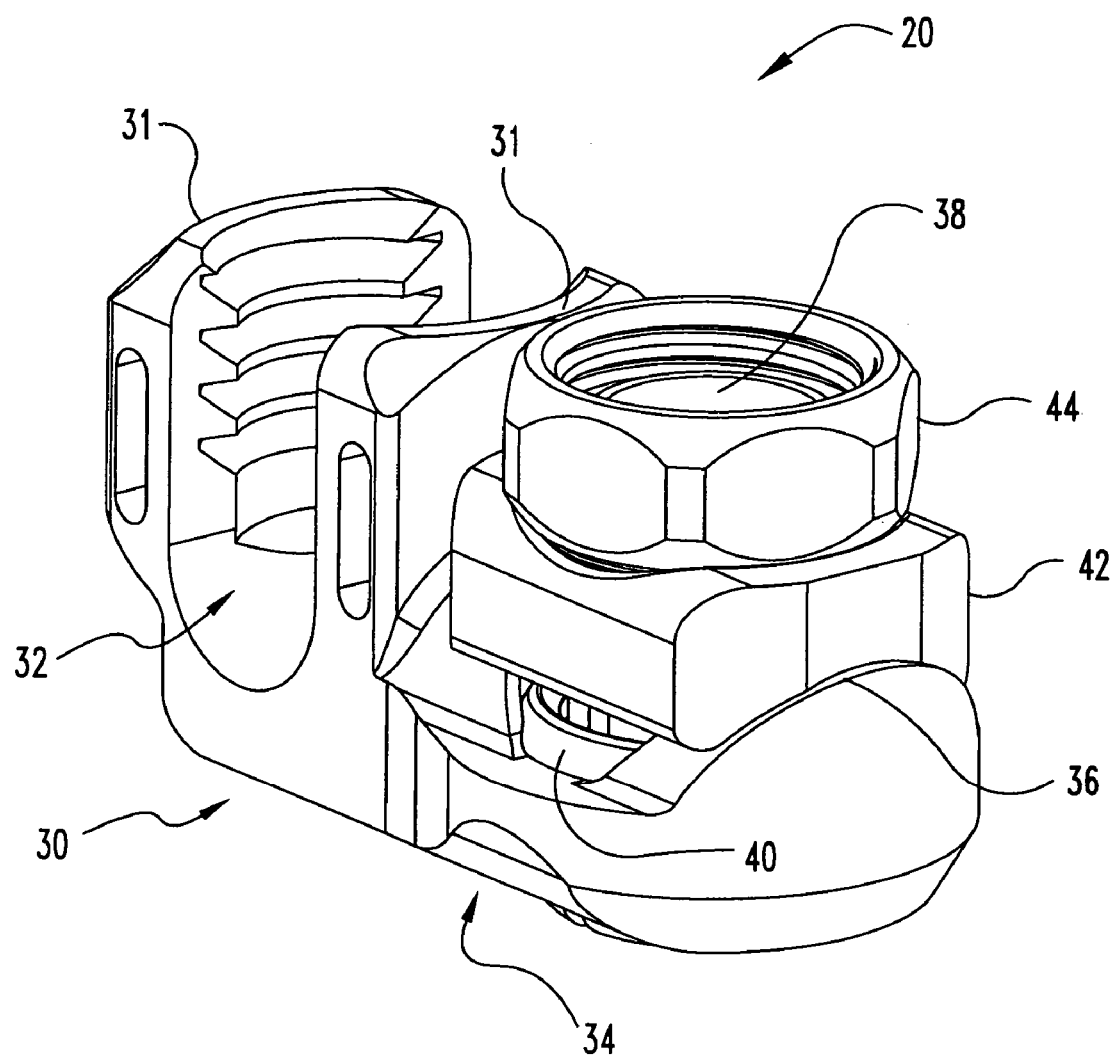
FIG. 2 is a perspective view of the connecting assembly according to the embodiment shown in FIG. 1.

Referring to FIG. 2, the illustrated embodiment of connecting assembly 20 includes a body 30 having two upright portions 31 defining a channel 32 configured to accommodate elongated member 24. The width of channel 32 is approximately the same as or slightly larger than the diameter of member 24, which allows easier insertion of member 24 in channel 32, allows for compensation for contouring of member 24, and also allows use of a range of member diameters or widths with the same channel 32. In another embodiment, channel 32 is configured to allow a snap-fit of member 24 therein. Body 30 further defines a hole 34 extending therethrough and configured for receipt of additional components of assembly 20. Body 30 includes concave extensions 36 to permit pivoting of implant 22, as will be explained further below. Connecting assembly 20 further includes a collet 38 to receive implant 22, a ring member 40 for insertion in hole 34, a washer 42 and a nut 44.

Figure 3:
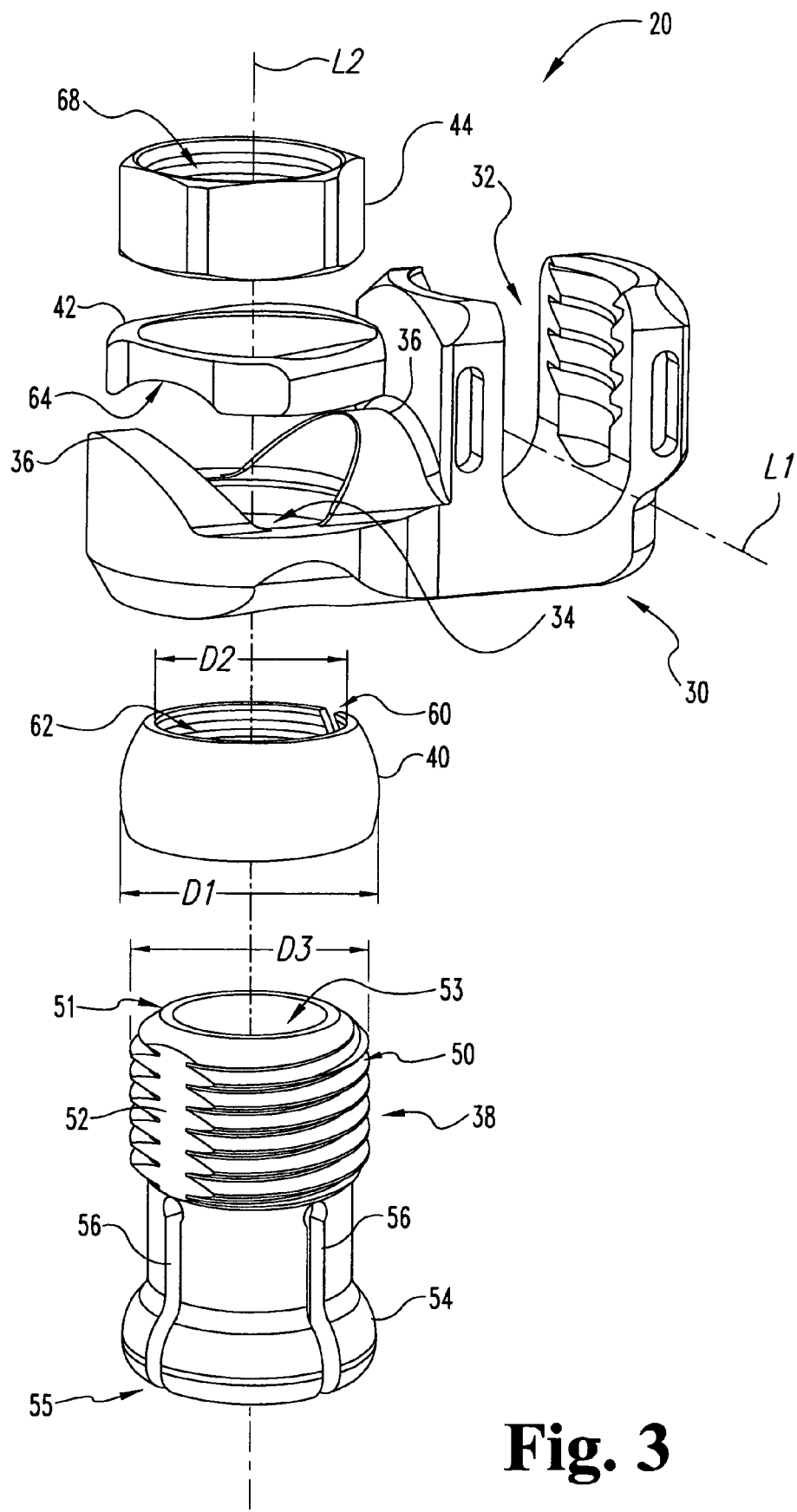
FIG. 3 is an exploded perspective view of the connecting assembly according to the embodiment shown in FIG. 2.

FIG. 3 is an expanded view of connecting assembly 20 to better illustrate the components of the illustrated embodiment. Channel 32 is substantially U-shaped with a longitudinal axis L1, with member 24 generally extending along longitudinal axis L1. Upright portions 31 can include internal threaded portions 33 to be threadedly coupled with a retaining member (not shown) to secure member 24 in channel 32. Internal threaded portions 33 can include reverse angle threads, i.e. a thread in which the forward face points downward and inward as disclosed in U.S. Pat. No. 6,296,642, incorporated herein by reference in its entirety. In an embodiment, the retaining member is a generally cylindrical set screw with external threads, but may alternatively be another type of holding or locking mechanism. In an embodiment in which member 24 is sized to snap-fit with channel 32, member 24 may be thereby self-secured in channel 32. However, it should be appreciated that member 24 can be secured in channel 32 by other appropriate methods as would generally occur to one skilled in the art. As illustrated, channel 32 is at least partially open along the longitudinal axis L1 to accommodate top loading of member 24. It should be appreciated that channel 32 can be configured and shaped differently as would generally occur to one skilled in the art.

Hole 34 extends through body 30 along longitudinal axis L2 and in the illustrated embodiment has a generally circular cross-sectional dimension. In one embodiment, hole 34 is substantially perpendicular to channel 34 and substantially parallel to upright portions 31. However, it should be appreciated that hole 34 can include other cross-sectional shapes, orientations and dimensions. Channel 32 and hole 34 are not in communication in the illustrated embodiment. Additionally, channel 32 and hole 34 could be positioned differently relative to each other in a manner that would maintain the functions of connecting assembly 20.

In the illustrated embodiment, collet 38 includes a threaded portion 50 along at least a portion of a proximal end 51. Threaded portion 50 includes one or more flat sections 52. In one embodiment, collet 38 includes two flat sections 52 positioned substantially diametrically opposite each other along the outside of collet 38. An aperture 53 extends through collet 38. Collet 38 further includes a convex section 54 adjacent a distal end 55, the function of which will be explained in greater detail below. Additionally, collet 38 includes one or more slots 56. In one embodiment, there are four slots 56 equally positioned about a circumference of collet 38 and which are generally parallel to aperture 53. Collet 38 is generally cylindrically shaped, except for flat sections 52, with a circular cross-sectional dimension. The outer cross-sectional dimension of collet 38 at convex section 54 is larger than an outer cross-sectional dimension of collet 38 at other points in the illustrated embodiment. Collet 38 is sized and shaped so as to fit and move easily within hole 34, a portion of ring member 40, washer 42, and nut 44. However, it should be appreciated that collet 38 can be configured or shaped differently in other embodiments.

Ring member 40 is generally annular, having a gap 60 to allow expansion and contraction of ring member 40, and including a threaded interior portion 62. Threaded interior portion 62 is configured to threadedly couple with threaded portion 50 of collet 38 to enable positioning of ring member 40 about a portion of collet 38. Ring member 40 has unstressed or natural outer diameter D1, i.e. a diameter measured when ring member 40 is under no contractive (gap-closing) or expansive (gap-opening) stress. Ring member 40 has an inner diameter D2 just slightly larger than an outer diameter D3 of threaded portion 50 of collet 38 to permit ring member 40 to engage collet 38. In the illustrated embodiment, washer 42 includes a concave lower surface 64 translatable along extensions 36 of body 30 to allow movement, such as pivoting, of collet 38 and implant 22 relative to body 30. Nut 44 includes threaded interior portion 68 configured to threadedly couple with threaded portion 50 of collet 38.

Figure 4:
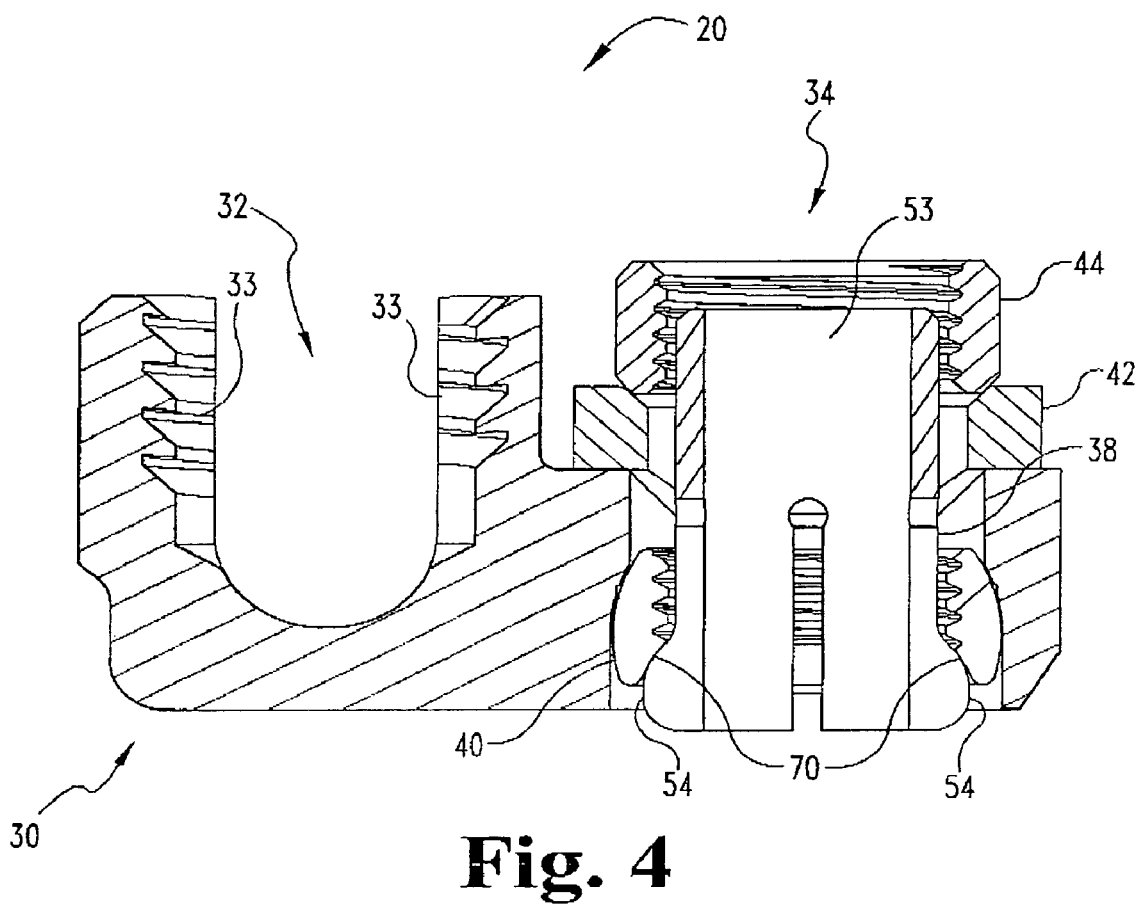
FIG. 4 is a cross-sectional view of the connecting assembly according to the embodiment shown in FIG. 2.

Referring to FIG. 4, there is shown a cross-sectional view of connector device 20 as assembled, including body 30, nut 44, washer 42, ring member 40, and collet 38. As illustrated in FIG. 4, ring member 40 includes a concave surface 70. In one embodiment, concave surface 70 is located on an inner lower surface of ring member 40. Concave surface 70 is configured to contact convex section 54 of collet 38 during operation of connector device 20, as will be explained in greater detail below.

Figure 5:
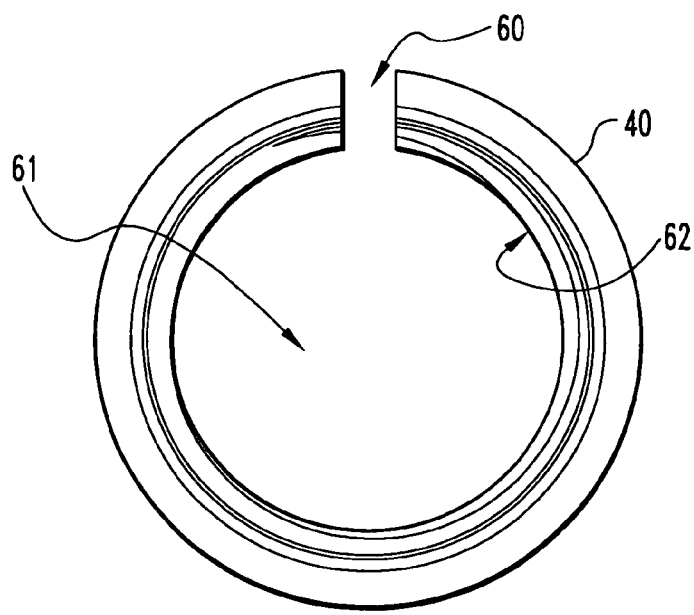
FIG. 5 is a top view of a component of the connecting assembly according to the embodiment shown in FIG. 2.

FIG. 5 is a top view of ring member 40 showing the illustrated embodiment of gap 60 and threaded interior portion 62. Ring member 40 defines an aperture 61 configured to receive a portion of collet 38. As stated above, threaded interior portion 62 of ring member 40 is configured to threadedly couple with threaded portion 50 of collet 38 to permit insertion of collet 38 in ring member 40.

Figure 6:
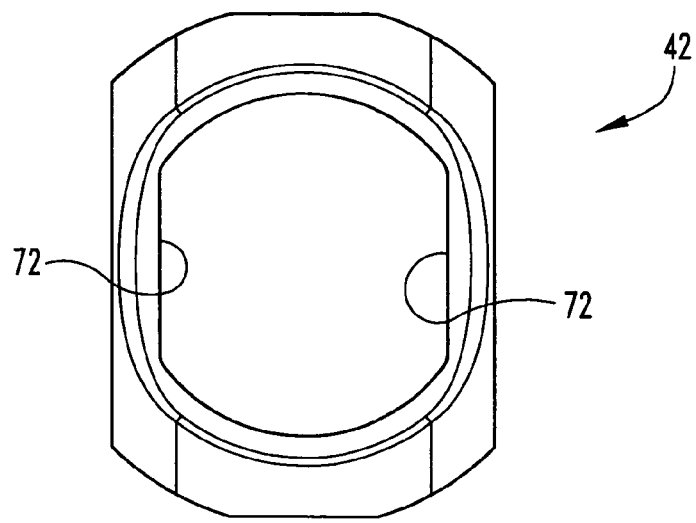
FIG. 6 is a top view of a component of the connecting assembly according to the embodiment shown in FIG. 2.

FIG. 6 is a top view of washer 42 illustrating interior flat surfaces 72. Flat surfaces 72 of washer 42 are configured to be adjacent or contact flat sections 50 of collet 38 to prevent rotation of collet 38 in hole 34 of body 30. In the illustrated embodiment, there are two flat surfaces 72. However, it should be appreciated that flat surfaces 72 could number more or less than two, but preferably there are the same number of flat sections 72 of washer 42 as the number of flat sections 52 of collet 38.

Generally referring to FIGS. 1-6, the operation and use of connecting assembly 20 will now be described with reference to a surgical procedure involving a section of spine. Annular ring member 40 is positioned about collet 38. In one embodiment, threaded interior portion 62 of ring member 40 is threaded about threaded portion 50 of collet 38 and then positioned adjacent or about collet 38 proximal convex section 54. However, it should be appreciated that annular ring member 40 and collet 38 can be joined in a different manner as would occur to one skilled in the art. Collet 38, with ring member 40 connected to it, is inserted into hole 34 in body 30. Alternatively, ring member 40 can be placed in hole 34 with collet 38 being inserted into ring member 40 and hole 34 substantially simultaneously. Washer 42 and nut 44 are placed about a portion of collet 38 that extends through hole 34 of body 30. In an alternative embodiment, washer 42 and nut 44 are placed about collet 38 after insertion of implant 22 therein. Assembly 20 may be assembled prior to use in a surgical procedure. However, it should be appreciated that in an alternative embodiment, connecting assembly 20 can be assembled during the surgical procedure.

To treat the condition or injury of the patient, the surgeon obtains access to the surgical site in a manner well known in the art, e.g. through incision and retraction of tissues. Once access to the surgical site has been obtained, e.g. via an opening such as a midline incision above the affected area, with tissue being resected laterally to the transverse process, or by other surgical procedure, the surgeon may connect one or more implants, such as bone screws, to adjacent or nearby vertebrae that require compression or distraction in order to relieve or improve their condition. For example, pilot holes in vertebrae, e.g. in pedicles, may be made, and screws may be inserted into or otherwise connected to two or more vertebrae. In one embodiment, implant 22 is inserted into a bony structure, such as vertebrae 26, at a desired position. A threaded portion of implant 22 can be threaded into bone to a desired depth. Implant 22 is received in aperture 53 of collet 38 to a position where collet 38 encompasses a desired section of implant 22. It should be appreciated that implant 22 can be inserted into a bony structure before or after insertion of implant 22 into collet 38. Additionally, implant 22 may be variably positioned in collet 38, for example with a substantial amount extending out of proximal end 51, or with little or none of implant 22 extending from proximal end 51. Connecting assembly 20 can be positioned at any of an infinite number of distances from vertebrae 26 along implant 22. Washer 42 permits pivoting of implant 22 and collet 38 relative to body 30, transverse to longitudinal axis L2, as a function of concave lower surface 64 of washer 42 being translatable along extensions 36 of body 30. In other words, washer 42 allows implant 22 to be positioned in any of a number of angular positions relative to body 30.

Nut 44 is threaded onto threaded portion 50 of collet 38 to secure implant 22 at the desired angular position. Tightening nut 44 moves collet 38 within hole 34 and secures contact of washer 42 against body 30. This movement of collet 38 expands ring member 40 to a limited position where ring member 40 is contacting an inner surface of hole 34. The expansion of ring member 40 is caused by movement of convex section 54 of collet 38 into ring member 40. Once ring member 40 reaches the limited position, further movement of collet 38 into ring member 40 causes contraction of collet 38 around implant 22 by way of slots 56. Concave surface 70 of ring member 40 facilitates movement of convex section 54 of collet 38 into ring member 40. The contraction of collet 38 around implant 22 locks implant 22 at the desired angular and/or translational position. Thereafter, member 24 is placed in channel 32 of body 30. Channel 32 is configured such that member 24 is loaded into channel 32 in a direction parallel to longitudinal axis L2 of hole 34. Additionally, a retaining member can be received in channel 32 of body 30 to secure member 24 therein. Further, member 24 can be received in another connecting assembly with an implant inserted into another vertebra to secure a section of vertebrae, as illustrated in FIG. 1.

Figure 7:
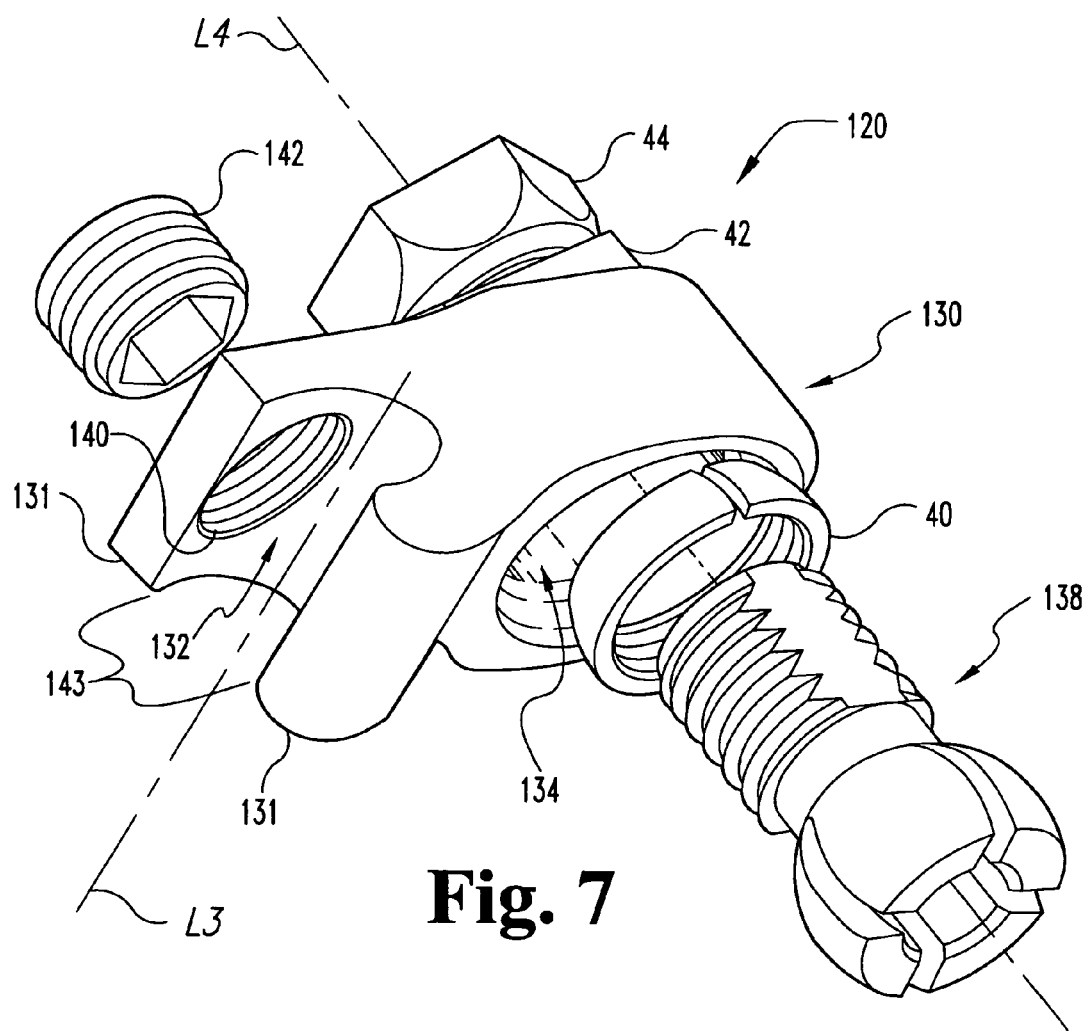
FIG. 7 is a perspective view of a connecting assembly according to another disclosed embodiment.

Referring to FIG. 7, there is shown an exploded view of another embodiment, where like reference numerals refer to like features previously discussed. Connecting assembly 120 includes a body 130 defining a hole 134 and including upright portions 131 defining a side loading channel 132 extending along longitudinal axis L3. Hole 134 extends through body 130 along a longitudinal axis L4 and has a generally circular cross-sectional shape. Additionally, in one embodiment, hole 134 is substantially perpendicular to channel 132. Similar to connecting assembly 20, the illustrated embodiment of connecting assembly 120 includes collet 38, ring member 40, washer 42, and nut 44. Connecting assembly 120 further includes a hole 140 in communication with channel 132. Hole 140 is configured for receipt of a retaining member 142. Retaining member 142 is operable to secure member 24 in channel 132. In one embodiment, retaining member 142 is a cylindrically shaped set screw with external threads. In an alternative embodiment, hole 140 is absent and retaining member 142 is received in channel 132 through an opening 143. However, it should be appreciated that member 24 can be secured in channel 132 by other appropriate methods as would generally occur to one skilled in the art, as discussed in connection with channel 32. Side loading channel 132 is configured, in one embodiment, such that member 24 is loaded into channel 132 in a direction substantially perpendicular to longitudinal axis L4 of hole 134.

In an alternative embodiment, ring member 40 is absent and movement of collet 38 in hole 34 and/or hole 134 is operable to secure collet 38 about implant 22. In another alternative embodiment, nut 44 and/or washer 42 are replaced with another such tightening mechanism as would generally occur to one skilled in the art.

The various components of connector device 20 are composed of biocompatible materials such as titanium, stainless steel, certain ceramics or plastics, or others.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed is:

1. An apparatus for connecting an implant with a rod, comprising:
    a body defining a first channel configured for receipt of the rod, said body further defining a second channel extending through said body, wherein a longitudinal axis of said first channel and a longitudinal axis of said second channel are substantially perpendicular, said rod extending along said longitudinal axis of said first channel;
    a collet positioned in said second channel, wherein said collet includes a longitudinal axis and defines an aperture extending entirely therethrough along said longitudinal axis of said collet configured for receipt of at least a portion of the implant, said collet being substantially cylindrically shaped, said collet having a portion including a convex section and one or more slots, said collet having a threaded portion including at least one flat section;
    an annular slotted ring member positioned in said second channel in an unstressed position and defining an aperture sized to allow insertion of at least a portion of said collet therethrough, said ring member having an inner portion including threads and an inner portion including a concave section configured to contact said convex section of said collet;
    a washer adjacent said second channel defining an aperture sized to allow insertion of at least a portion of said collet therethrough, said washer including at least one flat section configured to be adjacent said at least one flat section of said collet, wherein said washer includes a concave lower surface at least partially contacting and translating along said body to allow pivoting of said collet and washer relative to said body, wherein said collet is configured to pivot with the implant in said second channel to create a desired angular position of the implant relative to said body; and
    a nut adjacent said washer, said nut having threads adapted to connect with said upper threaded portion of said collet, whereby turning said nut moves said collet within said second channel,
    wherein said ring member is expandable by passage of at least a portion of said convex section of said collet with respect to said ring member, to the extent allowed by said second channel, whereby further passage of said convex section of said collet with respect to said ring member contracts said toilet around at least a portion of the implant to substantially lock the implant at a desired position.

2. The apparatus of claim 1, wherein the implant includes a longitudinal axis and the apparatus is positionable at varying locations along the longitudinal axis of the implant.

3. The apparatus of claim 1, wherein said longitudinal axis of said first channel and said longitudinal axis of said second channel are non-planar.

4. The apparatus of claim 1, wherein said first channel is positioned to accommodate loading of the rod in a direction parallel to said longitudinal axis of said second channel.

5. The apparatus of claim 1, wherein said first channel is positioned to accommodate loading of the rod in a direction perpendicular to said longitudinal axis of said second channel.

6. The apparatus of claim 1, wherein said first channel includes an inner threaded portion and is configured to receive a threaded retaining member to secure the rod in said first channel.

7. The apparatus of claim 1, wherein said body includes convex extensions proximal said second passage to fittingly contact said concave lower surface of said washer, said washer being translatable along said convex extensions.

8. The apparatus of claim 1, wherein said first channel is U-shaped, said first channel being at least partially open along said longitudinal axis of said first channel.

9. An apparatus for connecting an implant with a rod, comprising:
    a body defining a channel configured for receipt of the rod, said body further defining a hole extending through said body, wherein a longitudinal axis of said channel and a longitudinal axis of said hole are substantially perpendicular, said channel being at least partially open along said longitudinal axis of said channel;
    a collet, positionable in said hole, having a longitudinal axis and defining an aperture extending entirely therethrough along said longitudinal axis of said collet, the aperture being configured for receipt of at least a portion of the implant;
    an annular ring member, defining a gap, positionable in said hole in an unstressed position, said ring member further defining an aperture sized to allow insertion of at least a portion of said collet therethrough;
a pivoting member, positionable adjacent said hole, including a concave lower surface configured to at least partially contact and translate along said body, said pivoting member being configured to allow pivoting of said collet relative to said body, wherein said collet is configured to pivot with the implant in said hole to create a desired angular position of the implant relative to said body; and
a tightening member, positionable adjacent said pivoting member, adapted to connect with said collet to move said collet within said hole, whereby movement of said collet is operable to expand said ring member and contract said collet around at least a portion of the implant to secure the implant at a desired position.

10. The apparatus of claim 9, wherein said collet includes a convex section.

11. The apparatus of claim 10, wherein said ring member includes a concave section configured to fittingly contact said convex section of said collet.

12. The apparatus of claim 11, whereby movement of said collet within said hole includes drawing at least a portion of said convex section of said collet at least partially into said concave section of said ring member.

13. The apparatus of claim 9, wherein said collet is substantially cylindrically shaped and includes an upper threaded portion, a middle unthreaded portion, and a lower convex portion, said upper portion including at least one flat unthreaded section.

14. The apparatus of claim 13, wherein said pivoting member includes at least one inner flat section configured to fittingly contact said at least one flat unthreaded section of said collet to prevent rotation of said collet in said body.

15. The apparatus of claim 13, wherein said ring member includes an internally threaded portion configured to contact said upper threaded portion of said collet.

16. The apparatus of claim 13, wherein said tightening member includes an internally threaded portion configured to contact said upper threaded portion of said collet, whereby threading said tightening member along said upper threaded portion of said collet moves said collet within said hole.

17. The apparatus of claim 9, wherein said channel opens along said longitudinal axis of said channel in direction parallel to said longitudinal axis of said hole.

18. The apparatus of claim 9, wherein said channel opens along said longitudinal axis of said channel in direction perpendicular to said longitudinal axis of said hole.

19. A method, comprising:
placing an annular ring member with a slot around a collet, said annular ring member including an inner threaded portion configured to connect with a threaded upper portion of said collet to allow positioning of said ring member about said collet, said collet being substantially cylindrically shaped extending along a longitudinal axis and defining a hollow interior along said longitudinal axis;
inserting an implant in said hollow interior of said collet to a position where said collet encompasses a desired portion of the implant;
inserting said collet inside a first channel in a body;
inserting a distal threaded portion of the implant in a bony structure of a patient at a desired angular position;
aligning the implant at a desired angular position relative to said body;
placing a washer around said collet proximal said first channel of said body, wherein said washer includes a concave lower surface translatable along a set of convex extensions of said body to allow pivotal movement of said collet and said body, wherein said collet is configured to pivot with the implant in said first channel to create a desired angular position of the implant relative to said body;
tightening a nut down on the threaded upper portion of said collet, said nut contacting an upper surface of said washer, whereby said tightening moves said collet within said first channel and secures contact of said washer against said body, said ring member being expandable to a limited position in response to movement of a convex section of said collet into said ring member, said collet being contractible around the implant in response to further movement of said convex section of said collet into said ring member, to secure said collet around the implant and lock the implant at the desired angular position; and
placing a rod in a second channel of said body, wherein a longitudinal axis of said first channel and a longitudinal axis of said second channel are substantially perpendicular, wherein said second channel has a U-shaped cross-sectional dimension along said longitudinal axis of said second channel to accommodate placing the rod in said second channel.

20. The method of claim 19, further comprising placing said annular ring member in said first channel of said body, wherein said inserting said collet occurs substantially simultaneously with said placing said annular ring member around said collet.

21. The method of claim 19, wherein a direction from a bottom of said second channel toward an opening of said second channel along said longitudinal axis of said second channel is parallel to said longitudinal axis of said first channel, said direction being perpendicular to said longitudinal axis of said second channel.

22. The method of claim 19, wherein a direction from a bottom of said second channel toward an opening of said second channel along said longitudinal axis of said second channel is perpendicular to said longitudinal axis of said first channel, said direction being perpendicular to said longitudinal axis of said second channel.

23. A method, comprising:
providing a connection apparatus to connect a bone anchor and a rod, said connection apparatus including a body having a first channel to receive the bone anchor and a second channel to receive the rod, said connection apparatus further including a collet encompassing a portion of the bone anchor, an annular ring member with a slot defining an aperture sized to allow insertion of at least a portion of said collet, a washer with a concave lower surface, and a nut, wherein:
a longitudinal axis of said first channel and a longitudinal axis of said second channel are substantially perpendicular; and
said second channel is at least partially open along said longitudinal axis of said second channel to accommodate loading of the rod into said second channel;
placing said connection apparatus at a desired position on the bone anchor;
creating the desired angular relationship between the bone anchor and said body by translating said concave surface of said washer along said body and pivoting of said collet with the bone anchor in said first channel relative to said body; and
turning said nut along a threaded portion of said collet to move the collet within the first channel, whereby said body, said ring member, and said collet create an interference fit operable to lock the bone anchoring mechanism at a desired angular position relative to said body.

24. The method of claim 23, further comprising inserting the rod in said second channel.

25. The method of claim 24, further comprising securing the rod in said second channel with a retaining member.

26. The method of claim 23, wherein said collet includes one or more slots to facilitate contraction of said collet around the bone anchoring mechanism.

27. The method of claim 23, wherein said collet includes a convex section configured to fittingly contact a concave section of said ring member, said ring member being expandable to a limited position upon movement of said convex section of said collet into said concave section of said ring member, whereby said collet is contractible around the implant in response to further movement of said convex section of said collet into said concave section of said ring member.

* * * * *